United States Patent [19]

Taheri

[11] Patent Number: 5,011,945
[45] Date of Patent: Apr. 30, 1991

[54] CONTINUOUS PROCESS FOR THE PRODUCTION OF MALEIC ANHYDRIDE

[75] Inventor: Hassan Taheri, Naperville, Ill.

[73] Assignee: Amoco Corporation, Chicago, Ill.

[21] Appl. No.: 440,309

[22] Filed: Nov. 22, 1989

Related U.S. Application Data

[63] Continuation-in-part of Ser. No. 91,440, Aug. 31, 1987, abandoned, and a continuation-in-part of Ser. No. 194,137, May 16, 1988, abandoned.

[51] Int. Cl.$^5$ .............................................. C07D 307/60
[52] U.S. Cl. ..................................... 549/260; 549/259
[58] Field of Search .................................. 549/259, 260

[56] References Cited

U.S. PATENT DOCUMENTS

| | | |
|---|---|---|
| 4,342,699 | 8/1982 | Palmer et al. ........................ 549/259 |
| 4,649,205 | 3/1987 | Edwards et al. ..................... 549/260 |
| 4,795,818 | 1/1989 | Becker et al. ........................ 549/260 |

*Primary Examiner*—Bernard I. Dentz
*Attorney, Agent, or Firm*—Gunar J. Blumberg; William H. Magidson; Ralph C. Medhurst

[57] ABSTRACT

A continuous process for production of maleic anhydride is disclosed wherein maleic anhydride is produced in high yield and catalyst productivity is in the range of from about 0.12 to about 0.18 pounds of maleic anhydride produced per pound of catalyst per hour. The catalyst comprises vanadium-phosphorus-oxygen and a modifier, preferably molybdenum. The increased catalyst productivity substantially increases production rates without necessity for extensive equipment modification.

7 Claims, No Drawings

CONTINUOUS PROCESS FOR THE PRODUCTION OF MALEIC ANHYDRIDE

This application is a continuation in part of Ser. No. 091,440, filed Aug. 31, 1987, now abandoned, and Ser. No. 194,137, filed May 16, 1988 now abandoned.

FIELD OF THE INVENTION

This invention relates generally to the preparation of maleic anhydride by catalytic oxidation of hydrocarbons, particularly n-butane. More specifically, this invention relates to a method for obtaining high yield and continuously stable catalyst selectivity in continuous operation to obtain optimum yield, wherein catalyst productivity is at least 60% greater than catalyst productivity in an air oxidation once-through conventional method for production of maleic anhydride.

Continuous oxidation of hydrocarbons to prepare maleic anhydride is subject to a declining maleic anhydride yield because of loss of selectivity of the vanadium-phosphorus-based catalysts used in the process.

This invention particularly relates to the catalytic, vapor-phase oxidation of n-butane to maleic anhydride in the presence of a vanadium phosphorus catalyst wherein the oxidation is in a continuous recycle method using essentially pure oxygen as the oxidizing agent, a high yield is obtained, and catalyst productivity is at least 60% greater than in a continuous, once-through process using air as a source of oxygen. The catalyst comprises vanadium-phosphorus-oxygen and a modifier, preferably molybdenum. Increased catalyst productivity permits use of less catalyst per unit of product. Existing production capacity is accordingly substantially increased without substantial equipment modification.

BACKGROUND OF THE INVENTION

Catalytic vapor phase oxidation of n-butane to maleic anhydride in heat transfer, medium-cooled, tubular reaction zones is well-known. Typically, a gaseous feed comprising molecular oxygen, n-butane and ballast gas is passed over a fixed bed of oxidation catalyst in one or more reaction tubes at temperatures of about 300° C. (572° F.) to about 650° C. (1202° F.) and pressures of from about 10 to 75 psia. In general, catalysts for the oxidation of $C_4$ hydrocarbons to maleic anhydride are based on vanadium and phosphorus. The difficulty with phosphorus-vanadium metal-promoted catalysts is that they tend to deactivate very quickly. It has been found by prior investigators that, contrary to some common reactions wherein the catalyst loses activity with time and the temperature is raised to compensate and to maintain the desired activity, in the oxidation of butane to maleic anhydride with vanadium-phosphorus catalysts, catalyst activity increases and selectivity decreases, with consequent loss in yield of maleic anhydride and increased production of carbon oxides and water. Since the oxidation reaction is highly exothermic, increased catalyst activity tends to increase oxidation temperature with consequent further increase in catalyst activity and decreased selectivity. In order to maintain the desired reaction zone temperature, heat transfer medium such as an oil or molten salt is circulated around the reaction tube or tubes. Typically, temperature of the heat transfer medium is adjusted to provide adequate cooling at the hottest point of the reaction zone. Given the positive dependency of reaction rates on reactant concentrations, the hottest point of the reaction zone is located where the reactant concentrations are greatest. Ideally, the hottest point of the reaction zone is maintained at a temperature wherein concentration of reactants is at a level to provide maximum conversion of the reactants and maximum selectivity to maleic anhydride without thermal runaway.

At present, known commercial processes for producing maleic anhydride from n-butane can be characterized as once-through air-oxidation processes in that air is used as the source of molecular oxygen, and, owing to the nitrogen content of air, levels of nitrogen in the reaction zone effluent build up to such an extent that recycle of effluent, with or without separation of nitrogen from unreacted n-butane, is economically impractical. In view of the flammability of mixtures of n-butane and air, concentrations of n-butane in a once-through air-oxidation process are limited typically to about a maximum of 1.8 mole %. Due to the impracticality of recycling unreacted n-butane at very low concentrations, the unreacted n-butane typically is discarded, further reducing total yield from n-butane consumed.

Suggestions have been proposed in the prior art to prepare maleic anhydride from n-butane in a continuous method wherein n-butane concentrations are higher than in the above once-through air-oxidation process. Substantially pure (at least 95%) molecular oxygen is used, and the temperature of the hottest point of the reaction zone, the so-called "hot spot", is controlled by the heat transfer medium to provide cooling. Continuous phosphorus addition is taught to maintain yield.

U.S. Pat. No. 4,342,699 teaches a batch process for production of maleic anhydride comprising contacting n-butane-rich feed consisting essentially of n-butane, molecular oxygen and ballast gas with an oxidation catalyst comprising a co-metal promoted vanadium-phosphorus catalyst. The co-metal is zinc, bismuth, copper or lithium. The reaction was in a heat transfer, medium-cooled tubular reaction zone, containing a fixed bed of catalyst graded in terms of reactivity wherein (1) n-butane is oxidized at relatively low per pass conversions, (2) reactor effluent is withdrawn from the reaction zone and a major portion of maleic anhydride is separated therefrom, and (3) a major portion of the effluent remaining after separation is recycled to the reaction zone. The feed consists essentially of about 2 to 10 mole % n-butane, about 8 to 20 mole % molecular oxygen and a balance of inert gas or gases. Air is taught as used on process start-up until inerts in the recycle gas build up, although oxygen instead of air can be used. An effluent comprising maleic anhydride, oxygenated by-product, unreacted n-butane and oxygen, and inert gas or gases is withdrawn from the exit end of the reaction zone, maleic anhydride and oxygenated hydrocarbon by-products are separated therefrom, and the remaining effluent is separated into a purge stream that is removed at a rate that substantially compensates for the buildup of inerts in the reaction zone. A recycle stream is recycled to the reaction zone with addition of make-up gas comprising n-butane and molecular oxygen. Reported yields ranged from 61.2 wt. % to 91.4 wt. % with recycle using pure oxygen. Runs of limited duration were from 1 to 4 days. Yields of up to 91.4 wt. % were achieved only by periodic regeneration of the catalyst by passing carbon tetrachloride over the catalyst. Accordingly, yields of about 90 wt. % are achieved with intermittent process down periods for catalyst regeneration. U.S. Pat. No. 4,342,699 does not teach or suggest a continuous process of extended duration with consistent high yields of at least 90 wt. %. Despite the use of recycle, U.S. Pat. No. 4,342,699 does not teach or suggest a continuous process for oxidation of n-butane to maleic anhydride.

U.S. Pat. No. 4,649,205 teaches a continuous process using air as a source of oxygen for oxidation of n-butane to maleic anhydride wherein the catalyst is continuously regenerated by contacting it during the vapor-phase oxidation with a phosphorus compound and water. The feedstock contained from 0.2 to about 1.7 mole % butane. The reaction was on a once-through basis without recycle. Yields were increased by addition of phosphorous compounds from about 80 wt. % to about 92 wt. %.

U.S. Pat. No. 4,795,818 teaches the continuous addition of a phosphorus compound to maintain reaction temperature at a constant level. Recycle operation is simulated in Examples 6 and 7. Feed range was 2.4–5.5 vol. % n-butane, 10–12 vol. % oxygen and the balance nitrogen. The process comprised operating the process in the absence of added phosphorus compound at a preselected conversion to obtain a specific yield of maleic anhydride, determining the temperature of the reaction at that conversion and yield and thereafter maintaining the temperature substantially constant by controlled continuous addition of a volatile phosphorus compound to maintain the yield of maleic anhydride substantially constant. Operation was taught as on a single-pass basis for 600 hours. Catalyst operating temperature was taken at the outlet gas temperature. Conversion of butane was 25% with 65% selectivity to maleic anhydride. Nitrogen buildup in recycle was not disclosed. No provision was taught for recovery of n-butane in the effluent or recycle stream.

Despite the improvements reported in the above-described patents, these improvements are not entirely satisfactory from the standpoint of operation of a continuous process for long periods to prepare maleic anhydride from n-butane wherein recycle is required to recover unreacted n-butane. With recycle, impurities in the n-butane feed and carbon oxides from the oxidation reaction build up in the recycle stream to reduce oxygen partial pressure and reduce yield of desired product.

Although the prior art suggest that recycle of effluent from a maleic anhydride oxidation process, coupled with addition of a phosphorus compound in water, can result in a viable, long-term, continuous oxidation process, such has not been demonstrated heretofore wherein product yield and catalyst productivity are equal to or better than previously obtained product yields and catalyst productivity.

It has been found that continuous operation for extended periods to achieve high product yields of maleic anhydride and desirable catalyst productivity requires highly purified oxygen as the oxidizing agent, limitation of oxygen and n-butane in the feed stream to assure safety, limited conversion of oxygen and n-butane in the oxidation process to reduce production of carbon oxides as by-products, addition of a phosphorus compound and water to maintain catalyst selectivity, and use of a co-metal modified catalyst of vanadium-phosphorus-oxygen wherein the co-metal is preferably molybdenum.

The use of air as a source of oxygen in a continuous recycle oxidation process is not feasible because of nitrogen build-up in the effluent.

The presence of carbon monoxide in quantity in the recycle stream as an oxidation product, and its subsequent undesirable oxidation to carbon dioxide, liberates heat and increases reaction temperature with consequent increased hot-spot temperature and consequent possible runaway hot-spot exotherm. Accordingly, catalyst temperature control, within narrow limits, is required in a continuous process for oxidizing n-butane to maleic anhydride.

Highly pure oxygen as an oxidizing agent, instead of air, is required to limit the presence of nitrogen in the process effluent stream. Highly pure oxygen, however, can be present in the oxidation reaction only in limited amounts to limit the reaction of carbon monoxide to carbon dioxide with production of excess reaction heat, thus increasing reaction temperature and hot spot temperature. Conversion rates of oxygen and n-butane are hot-spot temperature dependent, i.e. a high hot-spot temperature increases conversion of oxygen and n-butane.

Use of co-metal modified catalyst of vanadium-phosphorus-oxygen wherein the co-metal is molybdenum is required for increased yield and catalyst productivity over that obtained with a commercially available catalyst. Catalyst selectivity requires addition of a phosphorus compound and water.

SUMMARY OF THE INVENTION

An improved continuous recycle process is disclosed for continuous oxidation of n-butane to maleic anhydride wherein product yields are high and catalyst productivity is within the range of from about 0.12 to about 0.18 measured in pounds of maleic anhydride produced per unit pound of catalyst per hour. The improved continuous recycle process demonstrates improvements in product yields and catalyst productivity over a continuous once-through air oxidation process of at least 60% based upon the same catalyst wherein the catalyst is continuously regenerated in both methods by continued addition of an alkyl ester of orthophosphoric acid. The improvements in yield and catalyst productivity are obtained by a continuous recycle method wherein reaction hot-spot temperature is within the range of from about 830° to about 900° F.; oxygen feed at process inlet is within the range of from about 10 to about 18 mole %; n-butane feed is within the range of from about 4 to 10 mole %; reaction oxygen conversion per pass is within the range of from about 30 to 70 mole %; n-butane conversion per pass is within the range of from about 20 to 35 mole %; concentration of carbon monoxide in process recycle stream is within the range of from about 35 to about 55 mole %; preferably from about 40 to 45 mole %; and concentration of carbon dioxide in process recycle stream is within the range of from about 35 to about 50 mole %, preferably from about 40 to 45 mole %. Preferred catalyst is a vanadium-phosphorus oxygen catalyst with a co-metal modifier, preferably molybdenum.

DETAILS OF THE INVENTION

According to the present invention, there is provided a continuous process for the vapor-phase oxidation of a C$_4$-hydrocarbon feedstock to produce maleic anhydride. Product yield and catalyst productivity are improved over a conventional once-through air oxidation method. In the process, a mixture of the hydrocarbon feedstock and an oxidizing medium comprising highly purified molecular oxygen, about 95% pure oxygen, is contacted with a co-metal modified vanadium-phosphorus-oxygen catalyst. The catalyst is continuously regenerated by contacting it during the process in the presence of water vapor with an alkyl ester of orthophosphoric acid having the formula $(RO)_3P=O$ wherein the R is hydrogen or a $C_1$ to $C_4$ alkyl radical, at least one R being a $C_1$ to $C_4$ alkyl radical. The said process comprises a continuous recycle method wherein catalyst (hot-spot) temperature is within a range of from about 830° F. to about 900° F., oxygen feed rate at process inlet is within the range of from about 10 mole % to about 18 mole %, preferably from about 14 mole % to about 16 mole %, n-butane feed is within the range of from about 4 mole % to about 10 mole %, preferably from about 4 mole % to about 6 mole %, reaction oxygen conversion per pass is within the range of from about 30 mole % to about 70 mole %, n-butane conversion per pass is within the range of from about 20 to 35 mole %, concentration of carbon monoxide in process effluent is within the range of from about 35 mole % to about 55 mole %, preferably from about 40 mole % to about 45 mole %, and concentration of carbon dioxide in process effluent is within the range of from about 35 mole % to about 50 mole %, preferably from about 40 mole % to about 45 mole %.

The catalyst that is employed in the process of the present invention is an oxidation catalyst. It comprises vanadium, phosphorus and oxygen and a co-metal modifier. Such a catalyst will contain the phosphorus and vanadium in a phosphorus-to-vanadium atomic ratio within the range of about 0.8:1 to about 2:1, preferably, within the range of about 1:1 to about 1.3:1. Oxygen will satisfy the stoichiometry of the catalyst.

A preferred catalyst comprises vanadium, phosphorus, oxygen, and a modifier, such as molybdenum. Molybdenum is a preferred modifier. Such a catalyst will contain the phosphorus and vanadium in a phosphorus-to-vanadium atomic ratio that is defined hereinabove. The preferred catalyst contains molybdenum as a modifier, the molybdenum-to-vanadium atomic ratio is within the range of about 0.001:1 to about 0.2:1, preferably within the range of about 0.01:1 to about 0.06:1.

The catalyst can be employed in one or more fixed beds. The size and shape of such fixed-bed catalyst are not critical, e.g., the catalyst can be in the shape of a cylinder, or even a hollow cylinder.

A vanadium-phosphorus-oxygen catalyst can be prepared in various ways. Typical examples of preparation are taught in U.S. Pat. Nos. 3,862,146; 4,361,501; 4,132,670; 4,043,943; 4,435,521; 4,497,958; and 4,515,904, which are incorporated by reference.

The above examples of catalyst preparation are only a few of the ways of preparing a vanadium-phosphorus-oxygen catalyst. Therefore, it is to be understood that the illustrations of catalyst preparations are not intended to limit the scope of the present invention.

As pointed out hereinabove, the vanadium-phosphorus-oxygen catalyst can be reactivated suitably by adding an alkyl ester of phosphoric acid continuously to the feed during the vapor-phase oxidation process. A solution of alkyl ester of orthophosphoric acid in water can be applied to the catalyst in a uniform manner. Obviously, such a method is particularly suitable in continuous processes which utilize multitubular reactors. In such a process, the alkyl ester, in an aqueous medium comprising about 0.01 wt. % to about 90 wt. % of the alkyl ester, is sprayed as a liquid into the feed gas stream that flows to the reactor. Such reactivation is conducted in situ without interrupting production or utilizing a hot oil vaporizer, which tends to decompose alkyl phosphates. Consequently, such an addition method is very advantageous. The catalyst is regenerated by contacting it during the vaporphase oxidation with water and an alkyl ester of orthophosphoric acid having the formula $(RO)_3P=O$, where R is hydrogen or $C_1$ to $C_4$ alkyl radical, at least one R being a $C_1$ to $C_4$ alkyl radical.

Typically, the alkyl ester is added in an amount within the range from about 0.1 to about 100,000 parts per million by weight (ppm wt) of the reactor feed gas stream. Preferably, the alkyl phosphate is added in the range of about 0.1 ppm wt to about 30 ppm wt of the reactor feed gas stream.

The alkyl ester of orthophosphoric acid, the phosphorus compound, is suitably triethylphosphate or trimethylphosphate. The preferred phosphorus compound is triethylphosphate (TEP).

For effective reactivation of the catalyst, the phosphorus compound is contacted with the catalyst in the presence of water. Suitably, water should be present in the reaction zone in an amount that will enable the phosphorus to be uniformly distributed throughout a relatively long bed of catalyst that is found in the process of the present invention. Typically, such amount will be attained if the feed moisture content at the reactor inlet is within the range of about 3,000 ppm wt to about 40,000 ppm wt, preferably, within the range of about 7,000 ppm wt to about 25,000 ppm wt.

Conveniently, the alkyl phosphate solution, i.e., the alkyl phosphate in a water medium comprising about 0.01 wt. % to about 90 wt. % alkyl phosphate and, more preferably, about 0.01 wt. % to about 50 wt. % alkyl phosphate, is contacted with the feed gas stream that flows into the reactor. The water and alkyl phosphate may be added separately to the feed gas stream that flows into the reactor. The water and alkyl phosphate may be added separately to the feed gas stream, if desired, instead of as a solution. Alternatively, the alkyl phosphate and the water may be added directly to the butane or hydrocarbon feed prior to the mixing of the hydrocarbon and oxidizing medium reactants.

In the continuous recycle method of operation of the instant invention, it is desirable that the recycle stream to the feed stream be constantly analyzed as to concentration of oxygen, carbon monoxide, carbon dioxide and n-butane in order to maintain the required concentrations of these components in the feed stream. It is essential that oxygen feed rate to the reaction zone be within the range of from about 10 mole % to about 18 mole % and that n-butane feed rate to the reaction zone be within the range of from about 4 mole % to about 10 mole %. The remainder of the feed to the reaction zone in continuous recycle operation comprises carbon oxides, i.e., recycle effluent of about 35 to 55 mole % carbon monoxide and from about 35 to about 50 mole % carbon dioxide.

In order to obtain increased yield of product the reaction is conducted on the hydrocarbon-rich side of the flammability envelop wherein the n-butane feed concentration is from about 4 mole % to about 10 mole %. However, such a feed rate leads to an increased catalyst (hot spot) temperature. The catalyst (hot spot) temperature is controlled by means of the triethylphosphate (TEP) that is added to maintain the catalyst performance.

The molar ratio of carbon monoxide to carbon dioxide in recycle effluent is a function of catalyst choice and feed of TEP but can range from about 0.5:1 to about 2.5:1. Because of heat generated by oxidation of carbon monoxide to carbon dioxide with attendant possible rise in reaction zone temperature, ratio of carbon monoxide to carbon dioxide is preferably at least 1:1 to about 1.16:1, or higher.

A continuous recycle method of operation is defined as a procedure wherein reaction zone effluent containing maleic anhydride, n-butane, carbon oxides and other by-products is separated into two streams, one containing maleic anhydride and by-products, the other containing unreacted n-butane and carbon oxides. The stream containing n-butane and carbon oxides is continuously recycled to the reaction zone. The continuous once-through method of operation is defined as a procedure wherein feed of n-butane and oxygen is continuous but unreacted n-butane in reaction effluent is not recovered and recycled.

The instant invented continuous recycle process for producing maleic anhydride comprises (A) contacting a feed comprising about 4 to about 10 mole % n-butane, 10 to about 18 mole % molecular oxygen, and a balance comprising carbon oxides, water and an alkyl ester of orthophosphoric acid having the formula $(RO)_3P=O$, wherein the R is hydrogen or a $C_1$ to $C_4$ alkyl radical, at least one R being a $C_1$ to $C_4$ alkyl radical, in a quantity that is sufficient to provide an amount of phosphorus that is effective in controlling the hot spot temperature with a co-metal modified vanadium-phophorus-oxygen oxidation catalyst in a heat transfer medium-cooled, tubular reaction zone maintained under oxidation conditions effective to yield a 20 to 35 mole % conversion per pass of n-butane and a 30 to 70 mole % conversion of oxygen, said catalyst being graded along at least a portion of the effective length of the reaction zone so as to provide minimum reactivity nearest the feed end of the reaction zone and maximum reactivity nearest the exit end of the reaction zone; (B) withdrawing from the reaction zone an effluent comprising maleic anhydride, by-product oxygenated hydrocarbons, carbon oxides, n-butane and oxygen; (C) separating a major portion of maleic anhydride and oxygenated hydrocarbon by-products from said effluent; (D) removing from the effluent remaining after recovery of maleic anhydride and oxygenated hydrocarbon by-products a purge stream at a rate substantially corresponding to the rate of build-up of inert gases in the reaction zone; and (E) recycling effluent remaining after removal of the purge stream to the reaction zone with addition of make-up gases comprising n-butane and oxygen, in quantities to maintain n-butane concentration at the reaction zone inlet of 4 to 10 mole % and oxygen concentration at 10 to 18 mole %. Water and an alkyl ester of orthophosphoric acid having the formula of $(RO)^3P=O$, wherein the R is hydrogen or a $C_1$ to $C_4$ alkyl radical, at least one R being a $C_1$ to $C_4$ alkyl radical, are added in quantities that are sufficient to maintain the required reaction zone temperature.

In greater detail, a typical heat transfer medium-cooled, tubular reaction zone employed according to this invention comprises one or more hollow tubes, preferably with length to diameter ratios ranging from about 25 to about 500, such tubes being encased within a shell containing circulating heat transfer medium. The tubes preferably are constructed of carbon steel or stainless steel although other materials having a high degree of mechanical strength, corrosion resistance and chemical inertness also are suitable. The shell that encases the tube or tubes can be constructed from any suitable material but preferably is made of a carbon steel. The shell is provided with heating means, for example, an external electric coil or heater, to heat the heat transfer medium to the desired startup temperature. Cooling means, such as a stream boiler, also are provided to maintain the heat transfer medium at the desired temperature during oxidation. Circulation of heat transfer medium around the tube or tubes is conveniently accomplished through the use of a stirrer, a pump and baffle arrangement, or other suitable means.

Heat transfer media useful according to this invention are well-known to persons skilled in the art and, in general, are materials that remain in the liquid state at process temperatures and have a relatively high thermal conductivity. Examples of useful media include various heat transfer oils and salts such as nitrates and nitrites of akali metals, the salts being preferred due to their higher boiling points. A particularly preferred heat transfer medium is a eutectic mixture of potassium nitrate, sodium nitrate and sodium nitrite which not only has a desirably high boiling point, but also a sufficiently low freezing point such that it remains in the liquid state even during periods of reaction zone shutdown.

Catalyst is loaded into the reaction tube or tubes in such a manner that reactivity increases over at least portion of the effective reaction zone length from minimum reactivity nearest the feed end of the reaction zone to maximum reactivity nearest the exit end. For purposes hereof, effective reaction zone length is defined as the catalyst-containing portion of the reaction zone. Preferably, effective length is at least about 75% of overall length, with any remaining length forming one or two substantially dead, e.g., catalyst free, zones at the feed and/or exit ends of the reaction zone. More preferably, effective reaction zone length makes up about 80 to about 100% of overall length. As between feed end and exit end dead zones, the former is preferred because it can serve as a preheating zone for the oxidation feed introduced into the reaction zone.

Oxidation according to this invention is carried out in the above described heat transfer medium-cooled, tubular reaction zone containing graded catalyst, wherein the catalyst is a co-metal modified catalyst comprising vanadium-phosphorus-oxygen, by introducing a feed consisting essentially of about 4 to about 10 mole % n-butane, about 10 to about 18 mole % molecular oxygen and a balance comprising carbon oxides into the feed end of the reaction zone maintained under conditions such that a 20 to 35 mole % conversion per pass of n-butane is attained and oxygen conversion per pass is within the range of from about 30 to about 70 mole %. Phosphate and water are added with the feed. An effluent, comprising maleic anhydride, by-product oxygenated hydrocarbons, unreacted n-butane and oxygen, and inert gas or gases, is withdrawn from the exit end of the reaction zone. Maleic anhydride and oxygenated hydrocarbon by-products, acetic acid, etc., are substantially separated therefrom after which the remaining effluent is separated into a purge stream, that is removed at a rate that substantially compensates for the build-up of inerts in the reaction zone, and a recycle stream, mostly unreacted n-butane and carbon oxides, that is recycled to the reaction zone with addition of make-up gas comprising n-butane and molecular oxygen. Build-up of carbon oxides in the recycle stream is reduced by the purge stream.

The composition of the oxidation feed employed according to this invention is important not only from the standpoint of attaining desirable yields of maleic anhydride, but also with respect to safe reaction zone operation. As indicated hereinabove, the feed contains levels of n-butane on the hydrocarbon-rich side of the flammability envelope.

The n-butane used according to this invention preferably is substantially pure, i.e., at least about 96%.

The molecular oxygen source used according to the invention has a substantial effect on productivity. Substantially, i.e., at least 95%, pure oxygen is essential. When substantially pure oxygen is used as the molecular oxygen source, the recycle gas stream comprises about 35 to about 55 mole % carbon monoxide, about 30 to about 50 mole % carbon dioxide and less than about 1 mole % nitrogen. If air is the molecular oxygen source, the recycle gas stream can comprise, undesirably, about 70 to about 85 mole % nitrogen, up to about 5 mole % carbon dioxide and about 1 to about 10 mole % carbon monoxide. For a feed containing a 5.5 mole % n-butane, 14 mole % oxygen and a balance of carbon monoxide and carbon dioxide in a molar ration of about 1.1:1, a safety margin of 1.2 mole % n-butane or 1.6 mole % oxygen exists with respect to the flammability limit.

The oxidation feed is introduced into the feed end of the reaction zone which is maintained under reaction conditions effective to attain a 20 to 35 mole % conversion per pass of n-butane. For purposes hereof, per pass conversion is defined as 100% times the number of moles of n-butane oxidized divided by the number of moles of n-butane in the feed. Per pass n-butane conversion rate ranges from about 20 to about 35 mole % in order to attain high ultimate conversions with good selectivity to maleic anhydride. Reaction conditions include temperature, pressure, space velocity, and others as discussed in greater detail hereinbelow.

Reaction zone temperature is from about 830° F. (443° C.) to about 900° F. (482° C.). It is desirable to preheat the oxidation feed to within about 100° C. of reaction temperature prior to passing the feed over that portion of the catalyst bed that is graded from minimum to maximum reactivity.

Reaction zone pressure is not critical although from a practical standpoint it is preferred to operate at about 10 to about 70 psia.

The oxidation feed is fed to the reaction and oxygen zone at a rate such that preferred per pass n-butane and oxygen conversions are attained. Depending upon equipment limitations, volumetric space velocity of the feed ranges from about 1000 to about 3000/hour per pass. Preferably, volumetric space velocity ranges from about 1500 to about 2500/hour as the same result in desirble productivity without excessive pressure drop from the feed end to the exit end of the reaction zone. At volumetric space velocities of about 1500 to about 2500/hour, per pass n-butane conversions typically range from about 20 to about 35 mole %, and oxygen conversions range from about 30 to about 60 mole %. Contact time in the reaction zone varies depending on space velocity and pressure and typically ranges from about 0.5 to about 5 seconds.

From the exit end of the reaction zone there is withdrawn an effluent comprising maleic anhydride, by-product oxygenated hydrocarbons, inert gas or gases and unreacted n-butane and oxygen. Primary by-product oxygenated hydrocarbons include acetic and acrylic acids. The effluent is passed to a separation zone in which maleic anhydride and by-product oxygenated hydrocarbons are substantially recovered. The remaining effluent is divided into purge and recycle streams and the latter is returned to the reaction zone together with make-up gas comprising oxygen and n-butane.

Separation of maleic anhydride and by-product oxygenated hydrocarbons from the reaction zone effluent can be accomplished by any suitable means. For example, the effluent can be scrubbed with an aqueous liquid, e.g., an aqueous solution of maleic acid, and the resulting scrubber solution dehydrated to convert maleic acid to the anhydride. Acetic and acrylic acids, also removed from the effluent by scrubbing, pass overhead during dehydration and can be recovered by fractionation, extraction or other suitable means.

Catalyst productivity of the instant invented process is measured in pounds of maleic anhydride produced per unit pound of catalyst per hour in the reactor. Increased catalyst productivity per unit time per unit time per unit of catalyst in the reaction zone means increased efficiency of the catalyst with reduced economic costs of production. As measured by catalyst productivity of the process, the efficiency of the catalyst has been found to be increased by means of the continuous recycle method operating within the parameters of the process by at least 60% over the once-through recycle method wherein the catalyst in the continuous recycle method and continuous once-through method is continuously regenerated by continuous addition of an alkyl ester of orthophosphoric acid. Overall yield of the process is improved over the overall yield of the continuous once-through method.

The following examples illustrate the present invention, it being understood that the examples are for purposes of illustration and not limitation.

EXAMPLE I

Comparison runs were made for extended periods of approximately 300 days each using air as oxygen source to determine the relative catalyst productivity of a commercially available vanadium-phosphorus-oxygen catalyst considered to be representative of commercial catalyst available and a vanadium-phosphorus-oxygen catalyst modified with molybdenum as a co-metal. The commercial catalyst was a Denka catalyst, manufactured by Linde, A. G., West Germany. The co-metal modified vanadium-phosphorus-oxygen-catalyst had a phosphorus-vanadium atomic ratio in the range of from about 0.8:1 to about 2:1 and a molybdenum-to-vanadium ratio of from about 0.001:1 to about 0.2:1, depending upon period of days in reaction service. Oxygen inlet concentration in air was in the range of from about 21.69 to about 21.89 mole %, n-butane inlet concentration was in the range of from about 1.46 to about 1.52 mole %, reaction catalyst (hot spot) temperature was in the range of from about 830° F. to about 900° F., salt temperature was in the range of from about 750° F. to about 800° F. VHSV was 2000/hr. Phosphorus and water were added during each run at a rate of 5 ppm (wt.) triethylphosphate per total reactor feed, including n-butane and air, and 10,000 to 20,000 ppm (wt.) water, respectively.

Results were as follows:

TABLE I

|  | Selectivity Mole % | Conversion Mole % | Overall Yield % | Catalyst Productivity |
|---|---|---|---|---|
| Commercial Catalyst | 62-64 | 82-83 | 90-92 | 0.67 |
| Mo-Modified Catalyst | 65-67 | 82-83 | 95-97 | 0.78 |

Note: Catalyst productivity is measured in pounds of maleic anhydride produced per pound of catalyst per hour.

The above results demonstrate the increased overall yield and catalyst productivity obtained with a co-metal modified vanadium-phosphorus-oxygen catalyst versus a commercially available vanadium-phosphorus-oxygen catalyst.

EXAMPLE II

Comparison process runs were made using a continuous once-through procedure and a continuous recycle procedure to prepare maleic anhydride using liquid n-butane and relatively pure oxygen as the feedstock. Catalyst activity was maintained by continuous addition of triethylphosphate at a level wherein molar ratio of carbon monoxide to carbon dioxide was at least 1:1, wherein the recycle effluent contained from about 35 to about 55 mole % carbon monoxide and from about 35 to about 50 mole % carbon dioxide. Oxygen feed rate was within the range of from about 10 mole % to about 18 mole % and n-butane feed rate was within the range of from about 4 mole % to about 10 mole %. Reaction hot spot temperature was controlled by a graded catalyst bed continuously regenerated by addition of an alkyl ester of orthophosphoric acid.

Liquid n-butane (97% pure) was vaporized and metered using a DP cell and a control valve. Oxygen or air and the recycle gas were metered and combined with the butane. Nitrogen was provided for purging the reactor during shutdowns. The combined reactor feed was preheated to about 350° F. prior to entering the reactor. The reactor tube had an inner diameter of 0.957 inch and equipped with an axial thermowell with an outer diameter of 0.312 inch. The reactor was 16 feet long with the catalyst bed occupying a length of 13.5 feet. The thermowell had radial supports at 2 feet intervals to keep it centered in the reactor. It contained a traveling thermocouple with eight elements spaced 2 feet apart. The thermocouple had 8 junctions and could be moved up and down at 2 foot intervals. This system gave a complete temperature profile of the catalyst bed.

The reactor tube was immersed in a stirred bath of molten salt. The outside of the bath was wrapped with electric heaters and insulation. The reactor effluent line was also heated to keep maleic anhydride from condensing. A control valve in the effluent line served to control the reactor pressure. A filter was provided upstream of the control valve to retain catalyst fines.

The reactor effluent gases were passed through two water scrubbers. In the primary scrubber, a 4 foot i.d. × 5 foot high glass column filled with ⅜ inch Intalox TM saddles. The effluent was scrubbed with a circulating aqueous solution of maleic acid. The bulk of the maleic anhydride was removed in this scrubber. The effluent gas from the primary scrubber was then bubbled through a secondary scrubber a 4 foot i.d. × 5 foot high glass column filled with ⅜ inch Intalox TM saddles. The secondary scrubber contained water. In the once-through operation, the effluent gas from the secondary scrubber was passed through a wet test meter before being purged to the atmosphere. In the recycle operation, some of the gas from the secondary scrubber (approximately 5% or less) was purged to remove the accumulated inert gases (mostly carbon oxides); the rest was recycled back to the reactor.

Three Gast Model DAA-101-GB diaphragm compressors were used in parallel in the recycle stream to pump and pressurize the recycle gases to the reactor. A surge tank downstream of the compressors served to smooth out the pressure fluctuations. The pressure of the surge tank was kept at 30 psig by throttling the compressor suction with a control valve. The surge tank effluent passed through a DP cell and control valve before entering the reactor.

In both the once-thru and the recycle operations, triethylphosphate (TEP) was added to the reactor feed by passing a slip stream of the reactor feed gas through a TEP reservoir. The amount of TEP addition was controlled by the temperature of the reservoir as well as the flow rate of the slip stream. In the once-thru runs, the slip stream was part of the air feed. In the recycle runs, the slip stream was part of the recycle gas. In the once-through operation, the moisture content of the feed was varied by passing the air feed through a water saturator. In the recycle operation, the moisture was introduced via the recycle gas which was already saturated with water from the scrubbers. In all the runs, the TEP and moisture concentrations in the total reactor feed were fixed respectively at 3 ppm and 10,000 ppm. to maintain the performance of the catalyst bed The unit was equipped with a gas chromatographic (GC) analyzer for reactor feed/effluent analysis, an on-line infrared (IR) analyzer for butane, and another analyzer for oxygen. Comparative data were obtained on the same bed of catalyst in the once-thru and in the recycle modes. Operation was switched several times between the two modes of operations so that any improvements in yield could be substantiated. All the runs were performed at a gas volume hourly space velocity of 2,000/hr.

The catalyst was 3/16 inch × 3/16 inch cylindrical pellets with 1/16 inch hole in the center of the pellets. The catalyst was a commercial catalyst, Denka, manufactured by Linde, A. G. West Germany, which comprised vanadium, phosphorus and oxygen. The catalyst had been pilot plant activated and conditioned for about 181 days prior. The catalyst was graded so the n-butane conversion could be well distributed across the length of the catalyst bed. The grading utilized the inert material Denstone TM of the same size as the catalyst pellets (3/16 inch cylinders). The bed was divided into three equal zones with each zone containing different amounts of the catalyst and the inert. The first zone consisted of a 50-50 mixture of catalyst and Denstone TM (55 inch long, 250 grams catalyst, 250 grams Denstone TM), the second zone a 75% catalyst-25% inert (55 inch long, 352 grams catalyst, 117 grams Denstone TM), and the outlet zone consisting of 100 % catalyst (425 grams catalyst). In all, 1,027 grams of catalyst were packed into the reactor. In addition to the active catalyst, the bed contained a 22 inch length of Denstone TM in the inlet section serving as a preheater zone and a 7 inch length of Denstone TM in the outlet of the reactor serving as support for the catalyst bed.

The calculations of the catalyst performance included its activity as measured by the reactant's conversions and its overall yield. The conversions of n-butane and oxygen were calculated from the GC analysis of the reactor feed/effluent streams. In the once-thru operation, the conversion of oxygen was not calculated because of its very excess quantities in the reactor feed. In the recycle operation, oxygen conversion per pass was calculated in addition to the n-butane conversion because of its limited quantity in the feed.

Yield determination was by the measurement of the total maleic anhydride (MAN) formed in a given operation in a specified time period. It involved a material balance on the two scrubber columns for maleic acid. The MAN produced in the reactor was calculated from the maleic acid data corrected for the presence of other by-product acids, namely, acetic, acrylic, and fumaric. The overall yield was subsequently determined from this figure and the amount of n-butane fed during a specified time period.

The recycle process was shown to increase the product yield across the catalyst bed to greater than 100 wt. %. This was more than 10 wt. % increase over the once-thru operation under identical feed gas throughputs. The unit productivity of the catalyst was increased to 0.137 lbs. MAN/hr. lb. catalyst. This was more than double the typical productivities observed in the once-through operation with the same catalyst.

The on-stream catalyst performance was successfully maintained with the application of the yield maintenance technology, that is, the continuous on-line treatment of the catalyst with triethylphosphate and moisture and maintenance of process parameters. Product yields were consistently maintained over 90 wt. %. Product yield and catalyst productivity can be further increased by use of a co-metal modified vanadium-phosphorus catalyst, wherein the co-metal is molybdenum, as demonstrated in Example I.

Performance and efficiency of the catalyst did not deteriorate with time. No measurable decrease in catalyst productivity occurred over a period of 47 days.

Oxidations were conducted over the course of several days. Feed compositions, mode of operation, reaction conditions and results are shown in Table II.

Catalyst productivity for the once-through method of operation was within the range of 0.06 to 0.09 pounds of maleic anhydride per pound of catalyst per hour and for the recycle method of operation was within the range of from about 0.13 to about 0.16 pounds of maleic anhydride per pound of catalyst per hour.

TABLE II

Performance of Graded Bed of Catalyst A[1]
in Once-Thru and Recycle Operations

| Mode of Operation | Days on Stream | Inlet Conc., Mole % | | Temperatures, Deg. F | |
|---|---|---|---|---|---|
| | | Oxygen | n-C4 | Salt | Catalyst |
| Once-thru | 225 | 21.89 | 1.50 | 776 | 830 |
| Once-thru | 226 | 21.91 | 1.51 | 777 | 834 |
| Once-Thru | 227 | 21.78 | 1.50 | 776 | 833 |
| Once-Thru | 228 | 21.83 | 1.50 | 782 | 833 |
| Once-Thru | 230 | 21.77 | 1.51 | 782 | 837 |
| Once-Thru | 231 | 21.81 | 1.52 | 781 | 840 |
| Once-Thru | 234 | 21.75 | 1.51 | 781 | 839 |
| Recycle | 237 | 15.37 | 5.44 | 753 | 855 |
| Recycle | 238 | 14.90 | 5.58 | 753 | 839 |
| Once-Thru | 240 | 21.72 | 1.46 | 780 | 850 |
| Once-Thru | 242 | 21.69 | 1.51 | 773 | 842 |
| Once-Thru | 245 | 21.84 | 1.49 | 775 | 836 |
| Once-Thru | 246 | 21.84 | 1.50 | 775 | 835 |
| Once-Thru | 247 | 21.83 | 1.51 | 774 | 833 |
| Once-Thru | 248 | 21.74 | 1.52 | 774 | 831 |
| Once-Thru | 249 | 21.75 | 1.51 | 774 | 829 |
| Once-Thru | 250 | 21.73 | 1.50 | 774 | 829 |
| Recycle | 251 | 14.97 | 5.10 | 755 | 844 |
| Recycle | 252 | 14.87 | 5.10 | 754 | 855 |
| Recycle | 253 | 15.11 | 5.09 | 755 | 862 |
| Recycle | 254 | 14.87 | 5.29 | 755 | 866 |
| Recycle | 256 | 15.36 | 5.15 | 755 | 865 |
| Recycle | 257 | 15.21 | 5.43 | 754 | 879 |
| Recycle | 259 | 15.30 | 5.44 | 755 | 847 |
| Recycle | 260 | 14.25 | 5.56 | 755 | 844 |
| Recycle | 264 | 14.73 | 5.58 | 755 | 847 |
| Once-Thru | 266 | 21.78 | 1.47 | 783 | 840 |
| Recycle | 267 | 16.59 | 4.53 | 760 | 834 |
| Recycle | 271 | 15.93 | 5.11 | 760 | 838 |
| Recycle | 272 | 15.74 | 4.96 | 760 | 836 |
| Once-Thru | 274 | 21.79 | 1.46 | 783 | 828 |
| Once-Thru | 275 | 21.80 | 1.47 | 783 | 825 |
| Once-Thru | 276 | 21.79 | 1.46 | 783 | 824 |
| Recycle | 280 | 16.11 | 4.85 | 764 | 839 |
| Recycle | 281 | 15.93 | 4.80 | 764 | 856 |
| Recycle | 282 | 15.31 | 4.63 | 765 | 870 |
| Recycle | 283 | 16.33 | 4.80 | 758 | 856 |
| Recycle | 284 | 16.36 | 5.10 | 748 | 859 |
| Recycle | 285 | 16.46 | 4.88 | 753 | 878 |
| Recycle | 286 | 15.28 | 5.50 | 753 | 881 |
| Recycle | 288 | 15.55 | 5.66 | 753 | 870 |
| Recycle | 289 | 15.23 | 5.51 | 757 | 867 |
| Recycle | 290 | 14.62 | 5.44 | 758 | 848 |
| Recycle | 292 | 14.86 | 5.30 | 758 | 831 |
| Recycle | 293 | 14.49 | 5.44 | 759 | 833 |
| Recycle | 294 | 14.30 | 5.60 | 759 | 835 |
| Recycle | 295 | 14.22 | 5.69 | 763 | 843 |
| Recycle | 296 | 14.58 | 5.30 | 763 | 844 |
| Recycle | 297 | 14.70 | 5.13 | 763 | 846 |
| Recycle | 298 | 14.43 | 4.97 | 766 | 851 |
| Recycle | 299 | 14.31 | 5.25 | 766 | 853 |
| Recycle | 300 | 13.86 | 5.31 | 769 | 849 |
| Once-Thru | 301 | 21.78 | 1.46 | 782 | 831 |
| Once-Thru | 302 | 21.76 | 1.47 | 783 | 838 |
| Recycle | 304 | 17.55 | 5.37 | 754 | 847 |
| Recycle | 305 | 16.71 | 8.89 | 744 | 850 |
| Recycle | 306 | 14.21 | 5.63 | 760 | 870 |
| Recycle | 307 | 13.59 | 6.12 | 766 | 894 |
| Recycle | 308 | 14.67 | 5.81 | 760 | 893 |

| Mode of Operation | Days on Stream | Conv./Pass, Mole % | | Overall Yield Wt. % |
|---|---|---|---|---|
| | | Oxygen | n-C4 | |
| Once-Thru | 225 | — | 79.1 | 83.8 |
| Once-Thru | 226 | — | 80.2 | 85.3 |
| Once-Thru | 227 | — | 81.0 | 85.4 |
| Once-Thru | 228 | — | 81.5 | 85.9 |
| Once-Thru | 230 | — | 82.6 | 86.8 |
| Once-Thru | 231 | — | 83.5 | 86.5 |
| Once-Thru | 234 | — | 83.8 | 88.2 |
| Recycle | 237 | 53.8 | 31.6 | 95.3 |
| Recycle | 238 | 49.1 | 34.1 | 95.0 |
| Once-Thru | 240 | — | 89.7 | 82.7 |
| Once-Thru | 242 | — | 85.7 | 83.4 |
| Once-Thru | 245 | — | 84.3 | 84.2 |
| Once-Thru | 246 | — | 83.9 | 85.8 |
| Once-Thru | 247 | — | 83.6 | 85.1 |
| Once-Thru | 248 | — | 83.5 | 84.2 |
| Once-Thru | 249 | — | 82.9 | 84.2 |
| Once-Thru | 250 | — | 82.7 | 83.9 |
| Recycle | 251 | 57.3 | 32.6 | 92.6 |
| Recycle | 252 | 56.0 | 32.0 | 97.8 |
| Recycle | 253 | 55.5 | 33.8 | 95.8 |
| Recycle | 254 | 56.8 | 31.8 | 101.8 |
| Recycle | 256 | 54.8 | 32.4 | 101.2 |
| Recycle | 257 | 56.0 | 33.0 | 99.7 |
| Recycle | 259 | 53.8 | 31.3 | 93.5 |
| Recycle | 260 | 56.2 | 30.0 | 95.5 |
| Recycle | 264 | 59.1 | 30.0 | 99.4 |
| Once-Thru | 266 | — | 83.5 | 80.1 |
| Recycle | 267 | 49.9 | 40.7 | 104.6 |
| Recycle | 271 | 53.1 | 33.5 | 98.2 |
| Recycle | 272 | 52.4 | 34.1 | 100.5 |
| Once-Thru | 274 | — | 79.2 | 79.6 |
| Once-Thru | 275 | — | 79.7 | 81.4 |
| Once-Thru | 276 | — | 80.0 | 80.9 |
| Recycle | 280 | 47.4 | 35.5 | 100.6 |

TABLE II-continued

Performance of Graded Bed of Catalyst A[(1)]
in Once-Thru and Recycle Operations

| Recycle | 281 | 54.7 | 32.7 | 97.7 |
|---|---|---|---|---|
| Recycle | 282 | 47.6 | 36.3 | 112.0 |
| Recycle | 283 | 46.2 | 34.6 | 106.2 |
| Recycle | 284 | 49.3 | 30.2 | 106.6 |
| Recycle | 285 | 47.9 | 33.4 | 95.8 |
| Recycle | 286 | 54.9 | 30.4 | 93.1 |
| Recycle | 288 | 54.0 | 27.2 | 95.8 |
| Recycle | 289 | 55.0 | 30.5 | 96.2 |
| Recycle | 290 | 55.5 | 31.1 | 91.6 |
| Recycle | 292 | 55.8 | 33.4 | 95.3 |
| Recycle | 293 | 57.9 | 32.4 | 94.9 |
| Recycle | 294 | 57.1 | 29.8 | 91.7 |
| Recycle | 295 | 60.0 | 31.9 | 104.0 |
| Recycle | 296 | 60.8 | 30.8 | 101.3 |
| Recycle | 297 | 59.0 | 33.3 | 98.1 |
| Recycle | 298 | 61.5 | 32.2 | 100.5 |
| Recycle | 299 | 62.0 | 29.9 | 98.8 |
| Recycle | 300 | 62.3 | 29.2 | 99.5 |
| Once-Thru | 301 | — | 74.1 | 75.3 |
| Once-Thru | 302 | — | 76.5 | 78.8 |
| Recycle | 304 | 45.9 | 29.8 | 105.2 |
| Recycle | 305 | 46.8 | 23.7 | 101.0 |
| Recycle | 306 | 60.1 | 24.6 | 96.6 |
| Recycle | 307 | 65.7 | 24.3 | 96.5 |
| Recycle | 308 | 58.6 | 28.6 | 90.0 |

[(1)]Feed contained TEP at a concentration of 3 ppm and moisture at a concentration of 10,000 ppm.
Tests were run at a VHSV of 2000 hr$^{-1}$.

What is claimed is:

1. A continuous process for the vapor-phase oxidation of a butane feedstock to produce maleic anhydride in high yield wherein catalyst productivity is within the range of from about 0.12 to about 0.18, measured in pounds of maleic anhydride produced per pound of catalyst per hour, which process comprises:
   (a) contacting a nonflammable reactor feed consisting essentially of about 4 to about 10 mole % n-butane, about 10 to about 18 mole % oxygen, and the balance carbon oxides, wherein ratio of carbon monoxide to carbon dioxide is at least 1:1, with an oxidation catalyst comprising vanadium-phosphorus-oxygen, and a co-metal comprising molybdenum, wherein phosphorus-to-vanadium atomic ratio is in the range of from about 0.8:1 to about 2:1 and molybdenum-to-vanadium atomic ratio is in the range of from about 0.001:1 to about 0.2:1;
   (b) oxidizing said n-butane in continuous recycle method in a reaction zone, said reaction zone having a feed end and an exit end, wherein volumetric space velocity is in the range of from about 1000 to about 3000/hour per pass, n-butane conversion to maleic anhydride per pass is in the range of from about 20 to 35 mole %, oxygen conversion per pass is from about 30 to about 70 mole %, reaction catalyst temperature is within the range of from about 830° F. to about 900° F., wherein an alkyl ester of orthophosphoric acid and water are continuously added to said reactor feed, and wherein said catalyst is graded along at least a portion of said reaction zone with minimum reactivity nearest the feed end of said reaction zone and maximum reactivity nearest the exit end of said reaction zone;
   (c) withdrawing from said reaction zone an effluent comprising maleic anhydride, by-product oxygenated hydrocarbons, carbon oxides, unreacted n-butane and oxygen;
   (d) separating a major portion of maleic anhydride and oxygenated hydrocarbon by-products from said effluent;
   (e) removing from said effluent remaining after recovery of maleic anhydride and oxygenated hydrocarbons a purge stream at a rate substantially corresponding to the rate of build-up of carbon oxides in the reaction zone; and
   (f) recycling effluent remaining after removal of the purge stream to the reaction zone with addition of make-up gases comprising n-butane and oxygen.

2. The process of claim 1 wherein said alkyl ester of orthophosphoric acid has the formula $(RO)_3P=O$ wherein R is hydrogen or a $C_1$ to $C_4$ alkyl radical, at least one R being a $C_1$ to $C_4$ alkyl radical.

3. The process of claim 1 wherein the amount of alkyl ester of orthophosphoric acid added to said process is in the range of from about 0.1 to about 100,000 ppm (wt.) of the said reactor feed and water is present in the reaction zone within the range of from about 3000 ppm (wt.) to about 40,000 ppm (wt.).

4. The process of claim 3 wherein said alkyl ester of orthophosphoric acid is added in the range of from about 0.1 ppm (wt.) to about 30 ppm (wt.) of said reactor feed and water is present in said reaction zone within the range of from about 7000 ppm (wt.) to about 25,000 ppm (wt.).

5. The process of claim 1 wherein said alkyl ester of orthophosphoric acid is selected from the group consisting of trimethylphosphate and triethylphosphate.

6. The process of claim 1 wherein said molybdenum-to-vanadium atomic ratio is in the range of from about 0.01:1 : to about 0.06:1.

7. The process of claim 1 wherein said oxygen conversion per pass is in the range of from about 40 to about 70 mole %.

* * * * *

UNITED STATES PATENT OFFICE
CERTIFICATE OF CORRECTION

Patent No. 5,011,945    Dated   April 30, 1991

Inventor(s)  Hassan Taheri

It is certified that error appears in the above-identified patent and that said Letters Patent is hereby corrected as shown below:

| Col. | Line | |
|------|------|---|
| 7 | 56 | "(RO)$^3$P=O should read --(RO)$_3$P=O-- |
| 9 | 56 | "desirble" should read --desirable-- |
| 13 | 22 | "Man/hr.1b." should read --MAN/hr./lb.-- |

Signed and Sealed this

Fifteenth Day of September, 1992

Attest:

DOUGLAS B. COMER

Attesting Officer    Acting Commissioner of Patents and Trademarks